United States Patent [19]

Lin

[11] 4,069,264
[45] Jan. 17, 1978

[54] PROCESS FOR DIRECTED CHLORINATION OF ALKYLBENZENES

[75] Inventor: Henry C. Lin, Grand Island, N.Y.

[73] Assignee: Hooker Chemicals & Plastics Corporation, Niagara Falls, N.Y.

[21] Appl. No.: 729,439

[22] Filed: Oct. 4, 1976

[51] Int. Cl.$^2$ ............................................. C07C 25/04
[52] U.S. Cl. ............................. 260/650 R; 252/429 R
[58] Field of Search ..................................... 260/650 R

[56] References Cited

U.S. PATENT DOCUMENTS

| 1,741,305 | 12/1929 | Jaeger | 260/650 R |
| 1,946,040 | 2/1934 | Stoesser et al. | 260/650 R |
| 3,226,447 | 12/1965 | Binj et al. | 260/650 R |
| 4,031,142 | 6/1977 | Graham | 260/650 R |
| 4,031,147 | 6/1977 | Graham | 260/650 R |

*Primary Examiner*—C. Davis
*Attorney, Agent, or Firm*—Peter F. Casella; William J. Crossetta, Jr.; Arthur S. Cookfair

[57] ABSTRACT

A process for the production of nuclear chlorinated alkylbenzenes comprises reacting, in the liquid phase, alkylbenzene with chlorine in the presence of a Lewis acid catalyst and a co-catalyst comprising a thianthrene compound or mixture of thianthrene compounds characterized by the formula:

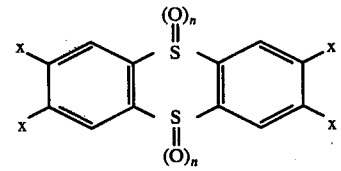

where each $n$ is 0 to 1, each $x$ is hydrogen or an electron-withdrawing substituent or an electron-donating substituent with the proviso that at least one $x$ is an electron withdrawing substituent and at least one $x$ is electron-donating substituent. A preferred co-catalyst is dimethyldichlorothianthrene. The monochlorinated alkylbenzene products prepared in this manner are characterized by a desirably low ratio of ortho to para isomer.

24 Claims, No Drawings

PROCESS FOR DIRECTED CHLORINATION OF ALKYLBENZENES

BACKGROUND OF THE INVENTION

The chemical reaction of chlorine with alkylbenzenes, such as toluene, to prepare nuclear substituted chloro-compounds such as monochlorotoluene, is well known and of considerable commercial importance. Such reactions are generally carried out in the presence of a chlorination catalyst such as antimony chloride, ferric chloride, aluminum chloride, and the like. The usual products of such reactions are a mixture of various mono-chlorinated and/or polychlorinated compounds and various positional isomers of these. For example, in the liquid phase substitution-chlorination of toluene, by reaction of chlorine and toluene, to form monochlorotoluene, the usual product is a mixture of orthochlorotoluene and parachlorotoluene which may, in addition, contain varying amounts of other chlorinated products such as metachlorotoluene, dichlorotoluene, polychlorotoluenes and benzylic chlorides. Of the major reaction products, that is orthochlorotoluene and parachlorotoluene, the latter is the most commercially valuable. In the past, considerable effort has been expanded in attempts to direct the chlorination reaction in such a manner as to lower the ratio of orthochlorotoluene to parachlorotoluene, that is, to discover reaction conditions under which the formation of parachlorotoluene is favored. Thus, for example, it is known from U.S. Pat. No. 1,946,040 that when alkylbenzenes are reacted with chlorine, the yield of parachlorinated product is improved with the aid of a mixed catalyst comprising sulfur and antimony trichloride and, optionally, iron or lead. In British Pat. No. 1,153,746 (1969) it is disclosed that in the chlorination of toluene in the presence of a ring chlorination catalyst, such as ferric chloride, antimony chloride, and the like, the ratio of orthochloro to parachloro isomers produced may be lowered by the presence of an organic sulfur compound such as thiophene, hexadecylmercaptan, dibenzothiophene or the like. Furthermore, in British Pat. No. 1,163,927 (1969) it is disclosed that the proportion of parachlorotoluene produced may be improved when toluene is chlorinated in the presence of elemental sulfur or an inorganic sulfur compound and a ring-chlorination catalyst such as ferric chloride, aluminum chloride, antimony chloride, zinc chloride, iodine, molybdenum chloride, stannous chloride, zirconium tetrachloride or boron trifluoride. In U.S. Pat. No. 3,226,447, issued Dec. 28, 1965 to Bing et al., it is disclosed that in the substitution-chlorination of benzene and toluene, the ratio of ortho isomer to para isomer in the chlorinated product may be lowered when the reaction is carried out in the presence of an iron, aluminum or antimony halide catalyst and a co-catalyst which is an organic sulfur compound wherein the sulfur is divalent. Examples of such co-catalyst include various mercaptans, mercapto-aliphatic carboxylic acids, aliphatic thiocarboxylic acids, alkyl sulfides, alkyl disulfides, thiophenols, aryl sulfides, aryl disulfides and the like containing divalent sulfur. The use of such co-catalysts in the chlorination of toluene produces a product wherein the ratio of orthochlorotoluene to parachlorotoluene is 1.2, indicating a considerable improvement over the ortho to para isomer ratio achieved in the absence of the co-catalyst. However, it will be apparent that even a 1.2 ratio of ortho to para isomer represents a considerable economic disadvantage in the production of substantial amounts — greater than 50 percent of the monochlorotoluene mixture — of the unwanted ortho isomer. Thus, it will be apparent that a considerable commercial benefit is to be derived from a still further lowering of the ortho to para isomer ratio.

Still further improvements in the preparation of monochlorotoluene having a low ortho to para isomer ratio are disclosed in co-pending applications Ser. No. 601,219, and Ser. No. 601,690 to John C. Graham, now U.S. Pat. Nos. 4,031,147 and 4,031,142, respectively. Co-pending application No. 601,690 discloses a process for the preparation of nuclear chlorinated alkylbenzenes, such as monochlorotoluene which comprises reacting an alkylbenzene, such as toluene, with chlorine in the presence of a Lewis acid catalyst and, as a co-catalyst, thianthrene. When toluene is chlorinated in accordance with the process disclosed in co-pending application Ser. No. 601,690, a monochlorotoluene product having an ortho to para isomer ratio of about 1.0 is obtainable.

In accordance with co-pending application Ser. No. 601,219, a monochlorotoluene product having an ortho to para isomer ratio of less than about 1.0 is obtainable with the aid of a co-catalyst comprising a thianthrene compound having electron-withdrawing substituents, such as chlorine, present on the nucleus thereof. Thus, in accordance with co-pending application Ser. No. 601,219, an alkylbenzene is reacted with chlorine in the presence of a Lewis acid catalyst and a co-catalyst comprising a thianthrene compound, or mixture of thianthrene compounds, characterized by the formula:

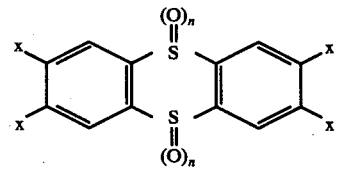

where each $n$ is 0 to 1, and each $x$ is hydrogen or an electron-withdrawing substituent.

Although the processes of co-pending application, Ser. No. 601,219 and Ser. No. 601,690 provide superior results to the prior art discussed above it will be apparent that still further improvements would be desirable and of commercial benefit. Furthermore, the co-catalyst, especially the chlorinated thianthrene cocatalyst of Ser. No. 601,219 is synthesized by a two-step reaction from a specific and limited selection of raw materials. Thus, it will be seen that an advantage is to be derived from the use of a co-catalyst that may be more easily synthesized from readily available raw materials.

It is an object of the present invention to provide an improved process for the directed nuclear chlorination of aromatic compounds. It is a further object to provide a process for the directed nuclear chlorination of alkylbenzenes, especially toluene, whereby the chlorinated product is characterized by a desirably low ratio of orthochloro to parachloro isomers. It is a still further object to provide an improved para-directing co-catalyst for such processes, that may be conveniently synthesized in a one step reaction, from readily available raw materials. It is a still further object to provide a novel catalyst system based on a para-directing co-catalyst comprising a thianthrene compound or mixture of thianthrene compounds, having both electron-withdrawing substituents and electron-donating substituents on the nucleus thereof.

The thianthrene compounds employed as para-directing co-catalysts in accordance with this invention are described hereinbelow in accordance with the current Chemical Abstracts system whereby the numbering of ring positions is as follows:

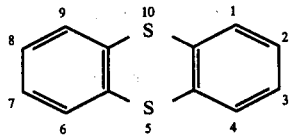

SUMMARY OF THE INVENTION

In accordance with the present invention there is provided a process for the production of nuclear chlorinated alkylbenzenes which comprises reacting, an alkylbenzene with chlorine in the presence of a catalyst system comprising a Lewis acid catalyst and a co-catalyst comprising a thianthrene compound or mixture of thianthrene compounds characterized by the formula:

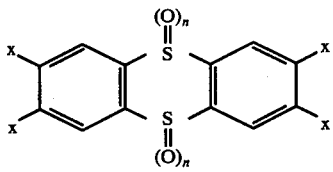

where each $n$ is 0 to 1, and each $x$ is hydrogen, or an electron-withdrawing substituent, or an electron-donating substituent, with the proviso that at least one $x$ is an electron-withdrawing substituent and at least one $x$ is an electron-donating substituent.

The co-catalysts suitable for use in the process of this invention are characterized by the formula shown hereinabove and include, for example, thianthrene compounds, as well as the analgous mono- or di-sulfoxide compounds, wherein one or more electron-withdrawing substituents and one or more electron-donating substituents are present in the positions designated, as well as mixtures of such compounds. When more than one electron-donating substituent is present on the thianthrene nucleus, the substituents may be the same or different. Suitable electron-donating substituents include, for example, alkyl and alkoxy groups. Preferably the electron-donating substituents are lower alkyl or alkoxy of 1 to 12 carbon atoms, and most preferably, methyl. When more than one electron-withdrawing substituent is present on the thianthrene nucleus, the substituents may be the same or different. Suitable electron-withdrawing substituents which may be present on the thianthrene or thianthrene oxide nucleus in the $x$ positions include for example, halo-, alkanoyl-, nitro-, sulfonyl-, cyano-, quarternary amino-, trifluoromethyl groups and the like, the preferred electron-withdrawing substituents being chloro-, fluoro-, bromo-, acetyl-, benzoyl, and trifluoromethyl. The most preferred co-catalyst of this invention is dimethyldichlorothianthrene.

The para-directing co-catalysts of the present invention differ substantially from the thianthrene co-catalysts of the prior art in that at least one electron-donating substituent is present on the thianthrene nucleus. Prior to the present invention it was considered that the presence of an electron-donating substituent on the thianthrene nucleus would be disadvantageous and would most likely diminish or negate the para-directing catalytic effect. Methylthianthrenes, such as 2,3,7,8-tetramethylthianthrene have been found to be substantially ineffective as para-directing co-catalysts when employed with a Lewis acid catalyst in the chlorination of toluene, giving ortho; para isomer ratios in the range of about 1.1 to 1.5. It is surprising therefore, in accordance with this invention to find that the presence of one or more electron-donating substituents, such as methyl substituents, at the 2,3,7, and/or 8 position of the thianthrene nucleus, actually enhances the para-directing catalytic activity of a thianthrene compound provided at least one electron-withdrawing substituent is also present at a 2,3,7, and/or 8 position.

In addition, the para-directing co-catalyst of the present invention provides a still further advantage over the prior art co-catalysts and especially over chlorothianthrenes, the preferred co-catalysts of the aforementioned patent application Ser. No. 601,219, in the method and materials from which it may be synthesized. The usual commercial preparation route for the preferred co-catalyst of that application is a two step process involving first the preparation of thianthrene from benzene and sulfur monochloride in the presence of aluminum chloride and, second, the catalyzed chlorination of thianthrene. The preferred method of preparation of the co-catalysts of the present invention is a one step process involving the reaction of an appropriately substituted compound of the benzene series with sulfur monochloride. It is an important advantage that the benzene series reactant utilized in the preparation of dimethyldichlorothianthrene - the preferred co-catalyst of the present invention - is orthochlorotoluene. This raw material is readily available in commercial quantities since it is a generally unwanted by-product of the preparation of parachlorotoluene. The thianthrene co-catalysts of the present invention may be prepared by various methods known in the art. Details for a preferred method of preparation are set forth in copending application Ser. No. 737,320, the disclosure of which is incorporated herein by reference.

The preferred co-catalysts of this invention are the thianthrene compounds and mixtures thereof characterized by the formula shown hereinabove where $n$ is $o$ and at least one $x$ is methyl and at least one $x$ is fluoro; chloro-, bromo- or trifluoromethyl, the most preferred being dimethyldichlorothianthrene. Typical preferred thianthrene co-catalysts of this invention include, for example, methyl chlorothianthrene, methylfluorothianthrene, methylbromothianthrene, methyltrifluoromethyl thianthrene, methyl dichlorothianthrene, methyl difluorothianthrene, methyl dibromothianthrene, methyl di(trifluoromethyl)thianthrene, methyltrifluoromethrene, methyltrichloro thianthrene, methyltribromothanthrene, methyltri(trifluoromethyl)thianthrene, dimethylmonofluorothianthrene, dimethylmonochlorothianthrene, dimethylmonobromothianthrene, dimethylmono(trifluoromethyl)thianthrene, dimethyldifluorothianthrene, dimethyldichlorothianthrene, dimethyldibromothianthrene, dimethyldi(trifluoromethyl)thianthrene, trimethylfluorothianthrene, trimethylchlorothianthrene, trimethylbromothianthrene trimethyl(trifluoromethyl)-thianthrene and the like and the various isomers thereof and mixtures of such compounds wherein the methyl, fluoro, chloro, bromo and/or trifluoromethyl substituents are present predominantly at the 2,3,7, and 8 positions of the thianthrene nucleus.

The preferred co-catalyst, dimethyldichlorothianthrene, includes any of the positional isomers thereof that conform to the formula shown hereinabove, such as 2,7-dimethyl-3,8-dichlorothianthrene; 2,8-dimethyl-3,7-dichlorothianthrene or 2,3-dimethyl-7,8-dichlorothianthrene. The preferred isomers are 2,8-dimethyl-3,7-dichlorothianthrene and 2,7-dimethyl-3,8-dichlorothianthrene. When dimethyldichlorothianthrene is prepared by the reaction of orthochlorotoluene and sulfur monochloride, the usual reaction product is a mixture wherein the predominant isomers are the 2,7-dimethyl-3,8-dichloro- and the 2,8-dimethyl-3,7-dichloro-isomers. It has been found both convenient and effective to utilize such mixtures as a co-catalyst in the process of this invention.

A wide variety of known Lewis acid catalysts may be employed in the process of the present invention. The term "Lewis acid catalyst" as employed herein includes, in addition to Lewis acids, those compounds or elements that will form or function as Lewis acids under the conditions of the chlorination reaction. Preferred catalysts for this purpose are compounds of antimony, lead, iron, molybdenum and aluminum, including for example, the halides, oxyhalides, oxides, sulfides, sulfates, carbonyls and elemental form of these elements and mixtures of such compounds and most preferably the chlorides, oxychlorides, oxides and elemental forms of antimony and iron. Typical of the catalysts which may be employed in the process of this invention are aluminum chloride, antimony trichloride, antimony pentachloride, antimony trioxide, antimony tetraoxide, antimony pentaoxide, antimony trifluoride, antimony oxychloride, molybdenum hexacarbonyl, lead sulfide, ferric chloride, ferrous chloride, ferrous sulfate, ferric oxide, ferrous sulfide, iron disulfide, iron pentacarbonyl, iron metal, and the like.

The amounts of catalyst and co-catalyst employed may vary considerably. Substantial benefits in terms of the lowering of the ratio of ortho- to para- isomer in the product may be achieved, for example, when the catalyst and co-catalyst are present in a total amount ranging from less than about 0.01 precent to about five percent by weight or more, based on the weight of alkylbenzene, and preferably in a molar ratio of catalyst:co-catalyst of about 0.01:1 to about 10:1. However, based on effectiveness as well as economic considerations, it is preferred to employ the catalyst and co-catalyst in a total amount of about 0.01 to about 2.0 weight percent, based on the weight of alkylbenzene and in a molar ratio of catalyst:co-catalyst of less than about 4:1 and most preferably about 0.10:1 to about 1:1.

Under atmospheric pressure, the chlorination reaction of the present invention may be carried out over a wide range of temperatures, ranging for example from sub-zero temperatures (Celsius scale) to over 100°Celsius The upper limit of temperature is, of course, determined by the boiling point of the reaction mixture, and may, depending on the boiling point limitation, range as high as 150°Celsius or higher. However, no practical advantage is gained through the use of higher temperatures and it is preferred to utilize temperatures in the range of about 0° to about 110° Celsius, and most preferably in the range of about 20° to about 70°Celsius. In general, the para-directing effect of the catalyst system will diminish at the extremes of these temperature ranges, depending on the particular catalyst system components employed and the amount and proportions thereof. The optimum temperature will vary somewhat, depending on the particular catalyst system employed. Thus, for example, to achieve the lowest ortho: para isomer ratio in the chlorinated product, the preferred process temperature is about 40° to about 50°Celsius when the catalyst system is dimethyldichlorothianthrene and antimony pentachloride. When the catalyst system is dimethyldichlorothianthrene and iron metal the preferred temperature is about 55° to about 65°Celsius. Although it is preferred to carry out the process at atmospheric pressures, subatmospheric or superatmospheric pressures may be employed if desired.

The alkylbenzenes which may be chlorinated in accordance with the present invention include the various straight chain and branched chain alkylbenzenes as well as substituted alkylbenzenes. The preferred alkyl benzenes are those wherein the alkyl group is 1 to 4 carbon atoms, and most preferably toluene. In the chlorination of toluene in accordance with this invention, monochlorotoluene products having a ratio of orthochlorotoluene/parachlorotoluene of less than about 1.0 are obtainable. It will be appreciated that, although the preparation of monochloro alkylbenzenes, having a relatively high proportion of parachloro alkylbenzene, is an important object of the present invention, the monochloro product may be further chlorinated, if desired, to produce higher chlorinated derivatives.

The process of this invention may be carried out by chlorination of the alkylbenzene in solution or in the absence of a solvent. Suitable solvents which may be employed, if desired, include for example various halogenated solvents such as carbon tetrachloride, or aromatic solvents such as monochlorobenzene. It is preferred, however, to carry out the chlorination directly, in the absence of a solvent.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE I

A mixture of 60 parts of sulfur monochloride and 162 parts of o-chlorotoluene was placed on an ice-water bath with stirring while 50 parts of aluminum trichloride was added slowly in small portions. The reaction mixture was heated on a water bath for 3 hours, then cooled, and a mixture of crushed ice and concentrated hydrochloric acid was added slowly. The mixture was steam-distilled for 3 hours. The solid residue in the flask was extracted with chloroform, and the chloroform extract was decolorized with activated carbon. Chloroform was then removed by evaporation and the remaining solid was recrystallized from acetone to give dimethyldichlorothianthrene, as a mixture of 2,7-dimethyl-3,8-dichloro-, and 2,8-dimethyl-3,7-dichloro isomers, in about 20% yield.

EXAMPLE 2

A mixture of 170 parts of toluene, 0.72 parts of dimethyldichlorothianthrene prepared as in Example 1, and 0.34 parts of antimony pentachloride was stirred on a water bath kept at 50° C, and a stream of chlorine (102 parts) was passed into the mixture over a period of about 7 hours. The reaction mixture was quenched with water, extracted with ether, washed with aqueous sodium bicarbonate, and dried over magnesium sulfate (anhydrous). A G.L.C. analysis of the reaction mixture indicated 15.8% of toluene, 38.0% orthochlorotoluene, 46.1% parachlorotoluene, and less than 0.1% of benzyl chloride, with an ortho:para isomer ratio of 0.82.

EXAMPLE 3

For purposes of comparison, procedure of Example 2 was repeated except that 0.84 parts of 2,3,7,8-tetrachlorothianthrene was substituted for the dimethyldichlorothianthrene. A G.L.C. analysis of the reaction mixture indicated 32.6% toluene, 32.3% orthochlorotoluene, and 35.1% parachlorotoluene, with an ortho:para isomer ratio of 0.92.

EXAMPLE 4

For purposes of comparison, the procedure of Example 2 was repeated except that 0.64 parts of 2,3,7,8-tetramethylthianthrene was substituted for the dimethyldichlorothianthrene and a total of 75 parts of chlorine was passed into the reaction mixture. A G.L.C. analysis of the reaction product indicated 39.5% toluene, 31.2% orthochlorotoluene, 27.6% parachlorotoluene, 1.4% benzyl chlorides, and 0.2% dichlorotoluene. The ratio of orthochlorotoluene:parachlorotoluene was 1.13.

EXAMPLE 5

For purposes of comparison, the procedure of Example 4 was repeated except that the reaction temperature was maintained at 30° C and a total of 58 parts of chlorine was passed into the reaction mixture. A G.L.C. analysis of the reaction product indicated 63.5% toluene, 20.5% orthochlorotoluene, 14.4% parachlorotoluene, 1.4% benzylchlorides, and 0.13% dichlorotoluene. The ratio of orthochlorotoluene:parachlorotoluene was 1.43.

From Examples 4 5, it will be seen that when thianthrene compounds having electron-donating substituents at the 2,3,7, and 8 positions are employed as para-directing co-catalysts in the chlorination of toluene, a relatively high ratio of ortho:para isomer results. When a thianthrene compound having electron-withdrawing substituents, such as chlorine at the 2,3,7, and 8 position is employed a substantially lower ortho:para isomer ratio in the product is achieved as in Example 3. Surprisingly, however, when a thianthrene compound, such as dimethyldichlorothianthrene, (Example 2) having both electron-donating and electron-withdrawing substituents present at the 2,3,7, or 8 position is employed, an improved para-directing effect is achieved with a still further lowering of the ortho:para isomer ratio.

EXAMPLES 6-11

The following examples illustrate the use of various Lewis acid catalysts and thianthrene compound co-catalysts in the chlorination of toluene in accordance with the present invention. The chlorination reactions were run in a manner substantially similar to the procedure of Example 2 except that the catalyst and co-catalyst and amounts of reactants were varied as shown. The dimethyldichlorothianthrene employed in Examples 10-12 as well as Examples 13-27 was prepared in the manner described in Example 1. The dimethyldifluorothianthrene employed in Examples 6 and 7 was a mixture of 2,7-dimethyl-3,8-difluoro- and 2,8-dimethyl-3,7 difluoro-isomers prepared in a manner similar to that of Example 1, except that o-fluorotoluene was substituted for o-chlorotoluene. The 2,7-dimethyl-3,8-dibromothianthrene employed in Examples 8 and 9 was prepared by reaction of p-thiocresol with 20% fuming sulfuric acid to form 2,7-dimethylthianthrene and subsequent reaction with bromine in glacial acetic acid. Analysis of the products was obtained by gas chromotographic techniques with the results as shown.

EXAMPLE 6

Antimony pentachloride catalyst and dimethyldifluorothianthrene co-catalyst were employed in a molar ratio of catalyst:co-catalyst of about 0.5.

| Reactants | Amount (Parts by weight) |
|---|---|
| Toluene | 170.0 |
| Dimethyldifluorothianthrene | 0.64 |
| SbCl$_5$ | 0.34 |
| Cl$_2$ | 56.0 |

The reaction product contained about 51.5 percent toluene, 22.1 percent orthochlorotoluene, and 26.3 percent parachlorotoluene. No benzylic products were detected. The ratio of ortho:para isomers was 0.84.

EXAMPLE 7

Ferric chloride catalyst and dimethyldifluorothianthrene co-catalyst were employed in a molar ratio of catalyst:co-catalyst of about 0.5.

| Reactants | Amount (Parts by weight) |
|---|---|
| Toluene | 170.0 |
| Dimethyldifluorothianthrene | 0.64 |
| FeCl$_3$ | 0.19 |
| Cl$_2$ | 71.0 |

The reaction product contained about 45.7 percent, 26.0 percent orthochlorotoluene, 28.0 percent parachlorotoluene, 0.2 percent dichlorotoluene and 0.1 percent benzyl chlorides. The ratio of ortho:para isomers was 0.93.

EXAMPLE 8

Antimony pentachloride catalyst and dimethyldibromothianthrene co-catalyst were employed in a molar ratio of catalyst:co-catalyst of about 0.5.

| Reactants | Amounts (Parts by weight) |
|---|---|
| Toluene | 170.0 |
| 2,7-Dimethyl-3,8-dibromothianthrene | 0.92 |
| SbCl$_5$ | 0.34 |
| Cl$_2$ | 71.0 |

The reaction product contained about 41.0 percent toluene, 26.7 percent orthochlorotoluene, 31.9 percent parachlorotoluene, 0.2 percent dichlorotoluene, and 0.2 percent benzyl chloride. The ratio of ortho:para isomers was 0.84.

EXAMPLE 9

Ferric chloride catalyst and dimethyldibromothianthrene co-catalyst were employed in a molar ratio of catalyst:co-catalyst of about 0.5.

| Reactants | Amounts (Parts by weight) |
|---|---|
| Toluene | 170.0 |
| 2,7-Dimethyl-3,8-dibromothianthrene | .92 |
| FeCl₃ | 0.19 |
| Cl₂ | 71.0 |

The reaction product contained about 31.8 percent toluene, 32.3 percent orthochlorotoluene, 35.6 percent parachlorotoluene and 0.3 percent dichlorotoluene. No benzyl chlorides were detected. The ratio of ortho:para isomers was 0.91.

EXAMPLE 10

Aluminum chloride catalyst and dimethyldichlorothianthrene co-catalsyt were employed in a molar ratio of catalyst:co-catalyst of about 1.0.

| Reactants | Amounts (Parts by weight) |
|---|---|
| Toluene | 170 |
| Dimethyldichlorothianthrene | 0.7 |
| AlCl₃ | 0.3 |
| Cl₂ | 67.0 |

The reaction product contained about 43.1 percent toluene, 26.7 percent orthochlorotoluene, and 30.2 percent parachlorotoluene. No benzyl chlorides were detected. The ratio of ortho:para isomers was 0.89.

EXAMPLE 11

Powered iron metal catalyst and dimethyldichlorothianthrene co-catalyst were employed in a molar ratio of catalyst:co-catalyst of about 1.0. The reaction temperature was maintained at about 60° C.

| Reactants | Amounts (Parts by weight) |
|---|---|
| Toluene | 200 |
| Dimethyldichlorothianthrene | 0.2 |
| Fe | 0.04 |
| Cl₂ | 55.0 |

The reaction product contained about 59.1 percent toluene, 19.1 percent orthochlorotoluene, 21.6 percent parachlorotoluene and 0.1 percent benzyl chlorides. The ratio of ortho:para isomers was 0.89.

EXAMPLE 12

Ferric chloride catalyst and dimethylchlorothianthrene co-catalyst were employed in a molar ratio of catalyst:co-catalyst of about 1:1.

| Reactants | Amounts (Parts by weight) |
|---|---|
| Toluene | 170. |
| Dimethyldichlorothianthrene | 0.17 |
| FeCl₃ | 0.05 |
| Cl₂ | 45 |

The reaction product contained about 56.0 percent toluene, 19.5 percent orthochlorotoluene, and 22.5 percent orthochlorotoluene. No benzylic products were detected. The ratio of ortho:para isomers was 0.87.

EXAMPLES 13–27

A series of chlorination reactions were run in a manner substantially similar to the procedure of Example 2 except that the temperature, catalyst:co-catalyst ratio, and amount of catalyst system employed were varied as shown in the table below. The catalyst system was antimony pentachloride catalyst and dimethyldichlorothianthrene co-catalyst. In the examples of the table, the amount of catalyst system employed is shown in weight percent, based on the amount of toluene. The reactions were run to various degrees of completion, as indicated by the percent toluene remaining in the product.

| Example | Weight Percent of Catalyst System | Molar Ratio Catalyst:Co-catalyst | Temperature (° C.) | Reaction Product (%) Toluene | Monochlorotoluene | α-Chlorinated Products | Ortho:Para Obtained |
|---|---|---|---|---|---|---|---|
| 13 | 0.06 | 0.2:1 | 60 | 51.9 | 48 | 0.1 | 0.83 |
| 14 | 0.06 | 0.2:1 | 43 | 58.7 | 41.3 | — | 0.78 |
| 15 | 0.06 | 0.2:1 | 30 | 59.3 | 39.3 | 1.3 | 0.95 |
| 16 | 0.06 | 0.2:1 | 0 | 80.9 | 17.2 | 1.9 | 1.44 |
| 17 | 0.06 | 0.5:1 | 80 | 47.7 | 52.3 | — | 0.90 |
| 18 | 0.06 | 0.5:1 | 60 | 29.3 | 70.6 | — | 0.85 |
| 19 | 0.06 | 0.5:1 | 50 | 15.9 | 84.1 | — | 0.82 |
| 20 | 0.06 | 0.5:1 | 40 | 24.4 | 75.5 | — | 0.81 |
| 21* | 0.06 | 0.5:1 | 20 – 25 | 13.8 | 86.0 | 0.4 | 0.90 |
| 22 | 1.0 | 1:1 | 60 | 50.4 | 49.5 | — | 1.12 |
| 23* | 1.0 | 1:1 | 30 | 51.0 | 48.8 | — | 0.82 |
| 24 | 1.0 | 1:1 | 0 | 60.3 | 39.6 | — | 0.97 |
| 25* | 0.08 | 0.17:1 | 60 | 60.5 | 39.2 | — | 1.39 |
| 26 | 0.08 | 0.17:1 | 0 | 62.6 | 37.3 | — | 1.08 |
| 27* | 0.06 | 5:1 | 60 | 54.3 | 45.2 | — | 1.62 |

*The product contained dichlorotoluene in the amounts of 0.2% in Examples 21 and 23; 0.3% in Example 25; and 0.5% in Example 27.

What is claimed is:

1. A process for the preparation of nuclear chlorinated alkylbenzenes which comprises reacting an alkylbenzene with chlorine in the presence of a Lewis acid catalyst and a co-catalyst comprising a thianthrene compound or mixture of thianthrene compounds characterized by the formula:

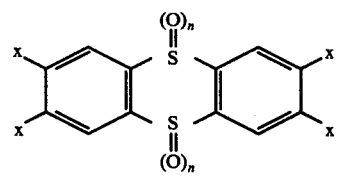

where each $n$ is 0 to 1 and each $x$ is hydrogen or an electron-withdrawing substituent or an electron-donating substituent with the proviso that at least one $x$ is an electron-withdrawing substituent and at least one $x$ is an electron-donating substituent.

2. A process according to claim 1 wherein said electron-donating substituent is an alkyl or alkoxy substituent.

3. A process according to claim 2 wherein said electron-withdrawing substituent is selected from the group consisting of fluoro-, chloro-, bromo-, acetyl-, benzoyl-, and trifluoromethyl.

4. A process according to claim 3 wherein the alkyl group of said alkylbenzene is a branched or straight chain alkyl group of 1 to 4 carbon atoms and said alkylbenzene is reacted with chlorine at a temperature of about 0° to about 150°0 Celsuis.

5. A process according to claim 4 wherein the Lewis acid catalyst is a halide, oxyhalide, oxide, sulfide, sulfate, carbonyl or elemental form of antimony, lead, iron, molybdenum, or aluminum.

6. A process according to claim 5 wherein the co-catalyst is a thianthrene compound or mixture of thianthrene compounds characterized by the formula shown wherein each n is 0.

7. A process according to claim 6 wherein the co-catalyst is a thianthrene compound or mixture of thianthrene compounds characterized by the formula shown wherein at least one x is an electron-donating substituent selected from a lower alkyl and lower alkoxy of 1 to 12 carbon atoms.

8. A process according to claim 7 wherein the Lewis acid catalyst is a chloride, oxychloride or elemental form of antimony or iron.

9. A process according to claim 8 wherein the co-catalyst is a thianthrene compound or mixture of thianthrene compounds characterized by the formula shown wherein the electron-withdrawing substituent is chloro-.

10. A process according to claim 9 wherein the co-catalyst is a thianthrene compound or mixture of thianthrene compounds characterized by the formula shown wherein at least one x methyl.

11. A process according to claim 10 wherein the alkylbenzene is toluene.

12. A process according to claim 11 wherein the co-catalyst is dimethyldichlorothianthrene.

13. A process according to claim 12 wherein the Lewis acid catalyst is SbCl$_5$.

14. A process according to claim 12 wherein the Lewis acid catalyst is FeCl$_3$.

15. A process according to claim 12 wherein the Lewis acid catalyst is Fe.

16. A process according to claim 12 wherein the Lewis acid catalyst is AlCl$_3$.

17. A process according to claim 11 wherein the co-catalyst is dimethyldifluorothianthrene.

18. A process according to claim 17 wherein the Lewis acid catalyst is SbCl$_5$.

19. A process according to claim 17 wherein the Lewis acid catalyst is FeCl$_3$.

20. A process according to claim 11 wherein the co-catalyst is dimethyldibromothianthrene.

21. A process according to claim 20 wherein the Lewis acid catalyst is SbCl$_5$.

22. A process according to claim 20 wherein the Lewis acid catalyst is FeCl$_3$.

23. A process for the preparation of monochlorotoluene which comprises reacting toluene with chlorine at a temperature of about 0° to about 110° Celsius, in the presence of a catalyst system comprising a Lewis acid catalyst selected from the group consisting of chlorides oxychlorides oxides and elemental forms of antimony and iron; and a co-catalyst comprising a thianthrene compound or mixture of thianthrene compounds characterized by the formula

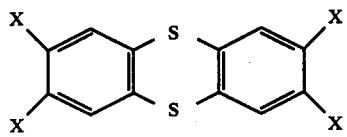

wherein each x is hydrogen, lower alkyl, or an electron-withdrawing substituent selected from the group consisting of fluoro-, chloro, bromo-, and trifluoromethyl-, with the proviso that at least one x is lower alkyl, and at least one x is an electron withdrawing substituent.

24. A process according to claim 23 wherein the catalyst system comprises about 0.01 to about 5 percent by weight, based on the amount of toluene, of antimony catalyst and dimethyldichlorothianthrene co-catalyst in a molar ratio of catalyst:co-catalyst of about 0.01:1 to about 10:1.

* * * * *

UNITED STATES PATENT OFFICE
CERTIFICATE OF CORRECTION

Patent No. 4,069,264             Dated January 17, 1978

Inventor(s) Henry C. Lin

It is certified that error appears in the above-identified patent and that said Letters Patent are hereby corrected as shown below:

Column 11, Claim 4, last line
"150° O Celsuis" should read --150° Celsius--.

Signed and Sealed this

Twenty-first Day of November 1978

[SEAL]

Attest:

RUTH C. MASON
Attesting Officer

DONALD W. BANNER
Commissioner of Patents and Trademarks